(12) United States Patent
Morency

(10) Patent No.: US 6,647,281 B2
(45) Date of Patent: Nov. 11, 2003

(54) EXPANDABLE DIAGNOSTIC OR THERAPEUTIC APPARATUS AND SYSTEM FOR INTRODUCING THE SAME INTO THE BODY

(75) Inventor: Steven Morency, Sunnyvale, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 204 days.

(21) Appl. No.: 09/827,611

(22) Filed: Apr. 6, 2001

(65) Prior Publication Data
US 2002/0147391 A1 Oct. 10, 2002

(51) Int. Cl.[7] .............................. A61B 5/04; A61B 1/00
(52) U.S. Cl. ........................ 600/374; 606/173; 600/139
(58) Field of Search ........................ 600/374, 139–152; 606/113, 110, 127, 170, 171

(56) References Cited

U.S. PATENT DOCUMENTS

| | | | |
|---|---|---|---|
| 5,309,910 A | | 5/1994 | Edwards et al. |
| 5,376,094 A | * | 12/1994 | Kline .......................... 606/113 |
| 5,741,286 A | * | 4/1998 | Recuset ....................... 606/170 |
| 5,961,513 A | | 10/1999 | Swanson et al. |
| 6,099,526 A | | 8/2000 | Whayne et al. |
| 6,142,994 A | | 11/2000 | Swanson et al. |
| 6,143,021 A | | 11/2000 | Staehle |
| 6,197,003 B1 | | 3/2001 | Howard, III et al. |
| 6,203,525 B1 | | 3/2001 | Whayne et al. |

FOREIGN PATENT DOCUMENTS

WO     WO 98/26724     6/1998

OTHER PUBLICATIONS

"Electrophysiology Catheters", EP Medsystems Ind., 1999.*

* cited by examiner

Primary Examiner—Thor Campbell
(74) Attorney, Agent, or Firm—Henricks, Slavin & Holmes LLP

(57) ABSTRACT

An assembly that includes an apparatus having an elongate body and an expandable/collapsible device, a tubular member defining a lumen configured to receive the apparatus, and a handle, fixedly connected to the elongate body and removably connected to the tubular member, configured to move at least one of the elongate body and the tubular member relative to the other.

27 Claims, 3 Drawing Sheets

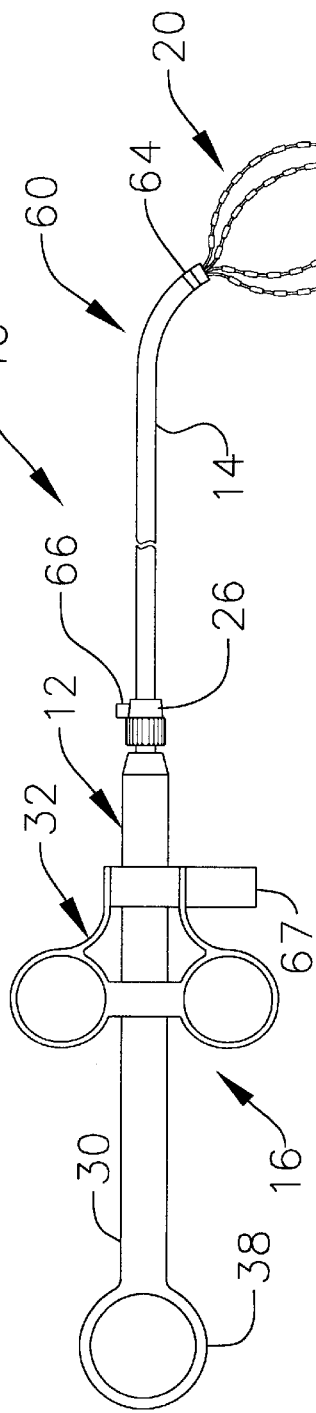
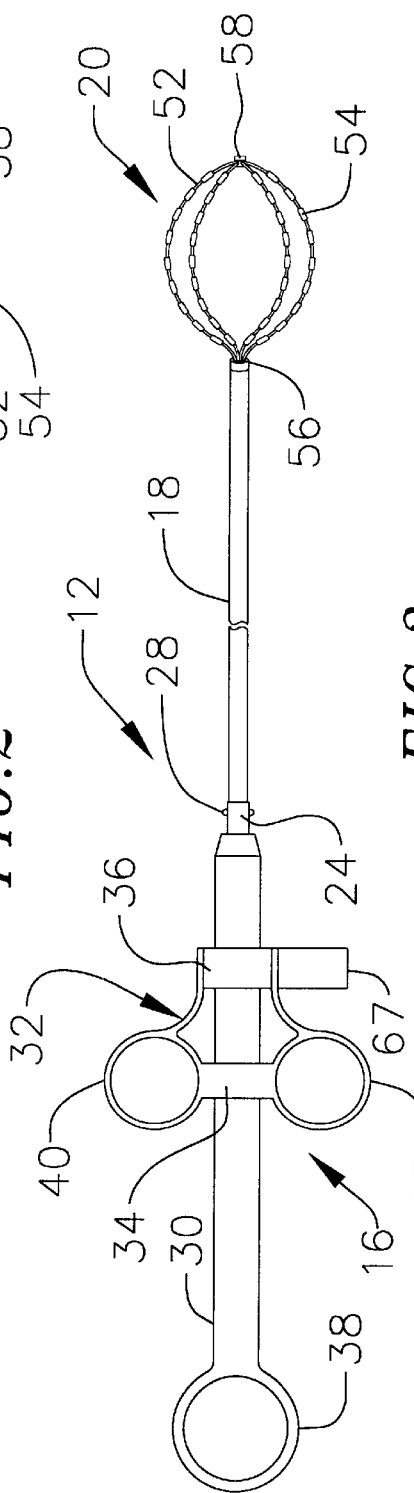
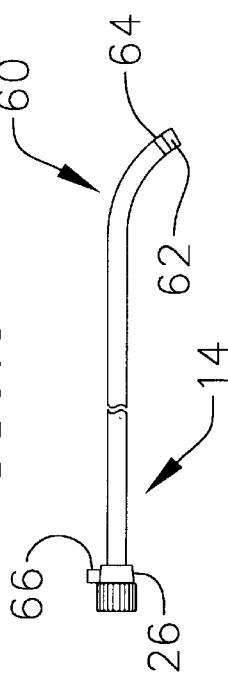

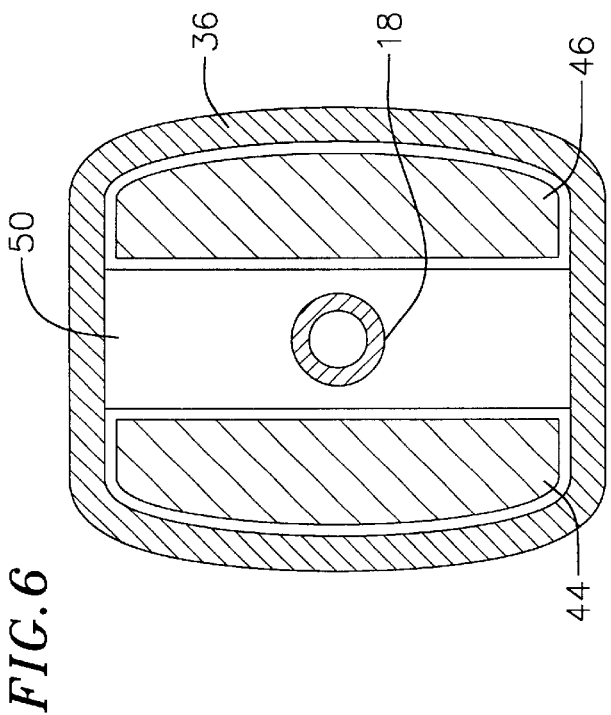
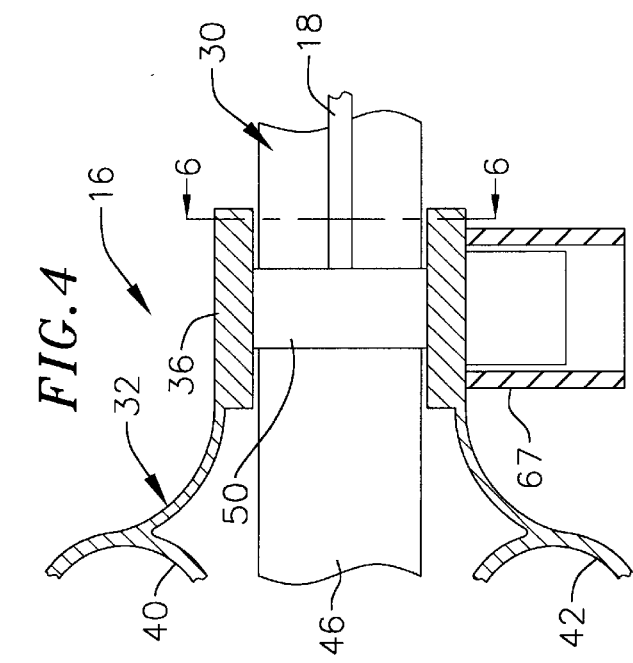
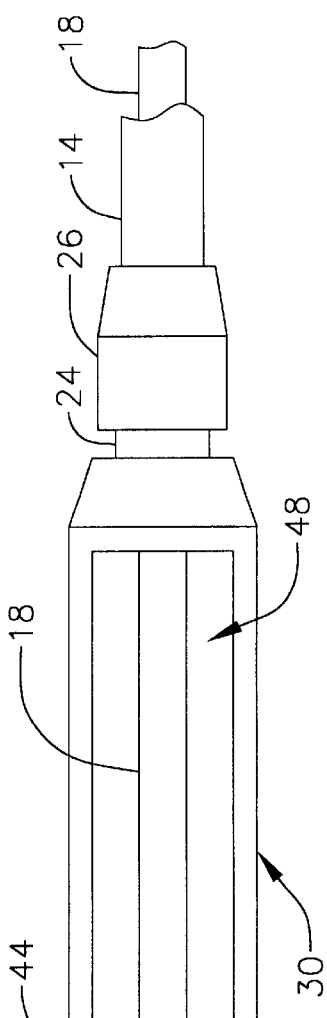
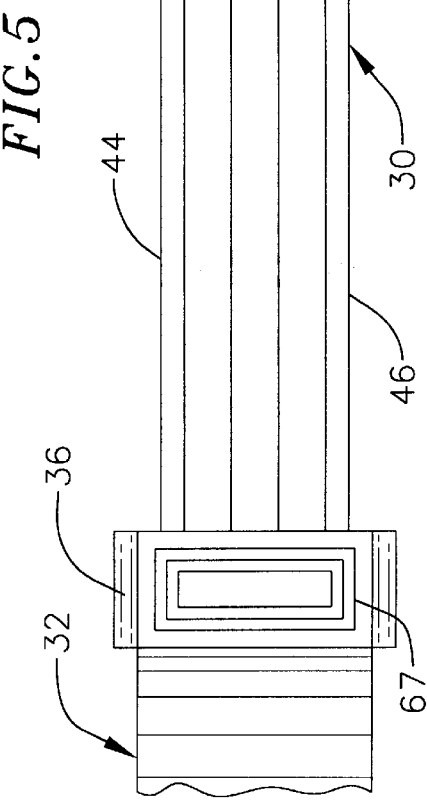

EXPANDABLE DIAGNOSTIC OR THERAPEUTIC APPARATUS AND SYSTEM FOR INTRODUCING THE SAME INTO THE BODY

BACKGROUND OF THE INVENTIONS

1. Field of Inventions

The present inventions relate generally to expandable diagnostic or therapeutic apparatus and the devices that are used to introduce expandable diagnostic or therapeutic apparatus into the body.

2. Description of the Related Art

There are many instances where physicians must introduce expandable diagnostic or therapeutic apparatus, such as three-dimensional mapping baskets and inflatable soft tissue coagulation structures, into the body. The diagnostic or therapeutic apparatus are often carried by catheters that allow physicians to gain access to the body in a minimally invasive manner by way of bodily lumens. In cardiac treatment, for example, a catheter is advanced through a main vein or artery into the region of the heart that is to be treated.

One method of introducing diagnostic or therapeutic apparatus into the body is to introduce a tubular member (typically a "sheath") into the vicinity of the target body region. The diagnostic or therapeutic apparatus is often positioned near the distal end of the sheath in a collapsed state as the sheath moves to the target region. Once there, the physician holds the sheath in place with one hand and advances the diagnostic or therapeutic apparatus with the other hand distally beyond the sheath where it expands into contact with tissue in the target region. Alternatively, the sheath may be advanced to the target region prior to the insertion of the diagnostic or therapeutic apparatus. Once the sheath is in place, the diagnostic or therapeutic apparatus is inserted through the sheath to the target region.

Precise placement of the diagnostic or therapeutic apparatus is very important and the distal regions of some conventional sheaths have a preset curvature which corresponds to a particular target region in order to facilitate the precise placement. With respect to cardiac mapping procedures, for example, as many as four different sheaths are used to facilitate precise placement in the four pulmonary veins. A variety of sheathes and basket catheters are separately sold and stored. The physician must select the sheaths for a particular procedure prior to the procedure itself.

The inventor herein has determined that the presently available apparatus for deploying expandable diagnostic or therapeutic apparatus is susceptible to improvement.

For example, the inventor herein has determined that the process of holding the sheath in place with one hand and while advancing the diagnostic or therapeutic apparatus with the other burdensome because it requires the use of both hands. One proposed solution would be to simply permanently couple the sheath and the diagnostic or therapeutic apparatus to a handle that moved the diagnostic or therapeutic apparatus relative to the sheath. Such an arrangement is illustrated in U.S. Pat. No. 5,309,910. The inventor herein has determined that, while useful, this permanently coupled arrangement precludes the use of multiple sheaths of differing preset curvature with the same diagnostic or therapeutic apparatus.

The inventor herein has also determined that another issue associated with presently available apparatus for deploying expandable diagnostic or therapeutic apparatus is convenience, i.e. it can be inconvenient to select, retrieve from storage, and prepare a variety of separately sold and stored devices prior to each procedure.

SUMMARY OF THE INVENTIONS

Accordingly, the general object of the present inventions is to provide a device that avoids, for practical purposes, the aforementioned problems. In particular, one object of the present inventions is to provide a device that makes it relatively easy for the physician to move a diagnostic or therapeutic apparatus relative to a sheath, without precluding the use of multiple sheaths with the same diagnostic or therapeutic apparatus. Another object of the present inventions is to provide an electrophysiological procedure kit that will eliminate the aforementioned inconvenience associated with separately sold and stored devices.

In order to accomplish some of these and other objectives, an assembly in accordance with one embodiment of a present invention includes an apparatus having an elongate body and an expandable/collapsible device carried by the distal portion of the elongate body, a tubular member defining a lumen configured to receive the apparatus, and a handle, fixedly connected to the elongate body and removably connected to the tubular member, configured to move at least one of the elongate body and the tubular member relative to the other.

The present assembly provides a number of advantages over conventional apparatus for deploying expandable diagnostic or therapeutic apparatus. For example, the present handle allows the physician to move the expandable/collapsible device relative to the tubular member with one hand.

Moreover, because the tubular member is removably secured, a variety of tubular members can be used with the same handle and expandable/collapsible device.

In order to accomplish some of these and other objectives, an electrophysiological procedure kit in accordance with one embodiment of a present invention includes a plurality of tubular members defining a different predetermined characteristic (such as distal portion curvature) and an electrophysiological apparatus including an elongate body, an expandable/collapsible device carried by the elongate body, a handle fixedly connected to the proximal portion of the elongate body and configured to be individually removably connected to the proximal portions of the tubular members. The handle is configured to move the elongate body and a removably connected tubular member relative to one another.

The kit may be provided with all of the tubular members required for a particular set of procedures involving the electrophysiological apparatus such as, for example, mapping the chambers of the heart. One advantage of such a kit is convenience in that opening a ready to use kit is far more convenient than collecting a number of separately sold and stored devices and preparing them for the procedure. Moreover, the electrophysiological apparatus may be positioned within the first tubular member that will be used in the procedure during assembly of the kit to further increase the convenience for the physician.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 1 is a plan view of a probe assembly including a diagnostic and/or therapeutic apparatus and a tubular member in accordance with a preferred embodiment of a present invention.

FIG. 2 is a plan view of the diagnostic and/or therapeutic apparatus illustrated in FIG. 1.

FIG. 3 is a plan view of the tubular member illustrated in FIG. 1.

FIG. 4 is a side, partial section view of a portion of the diagnostic and/or therapeutic apparatus handle illustrated in FIGS. 1 and 2.

FIG. 5 is a bottom view of a portion of the probe assembly illustrated in FIG. 1.

FIG. 6 is a section view taken along line 6—6 in FIG. 4.

DETAILED DESCRIPTION OF THE PREFERRED EMBODIMENTS

Figure 7:
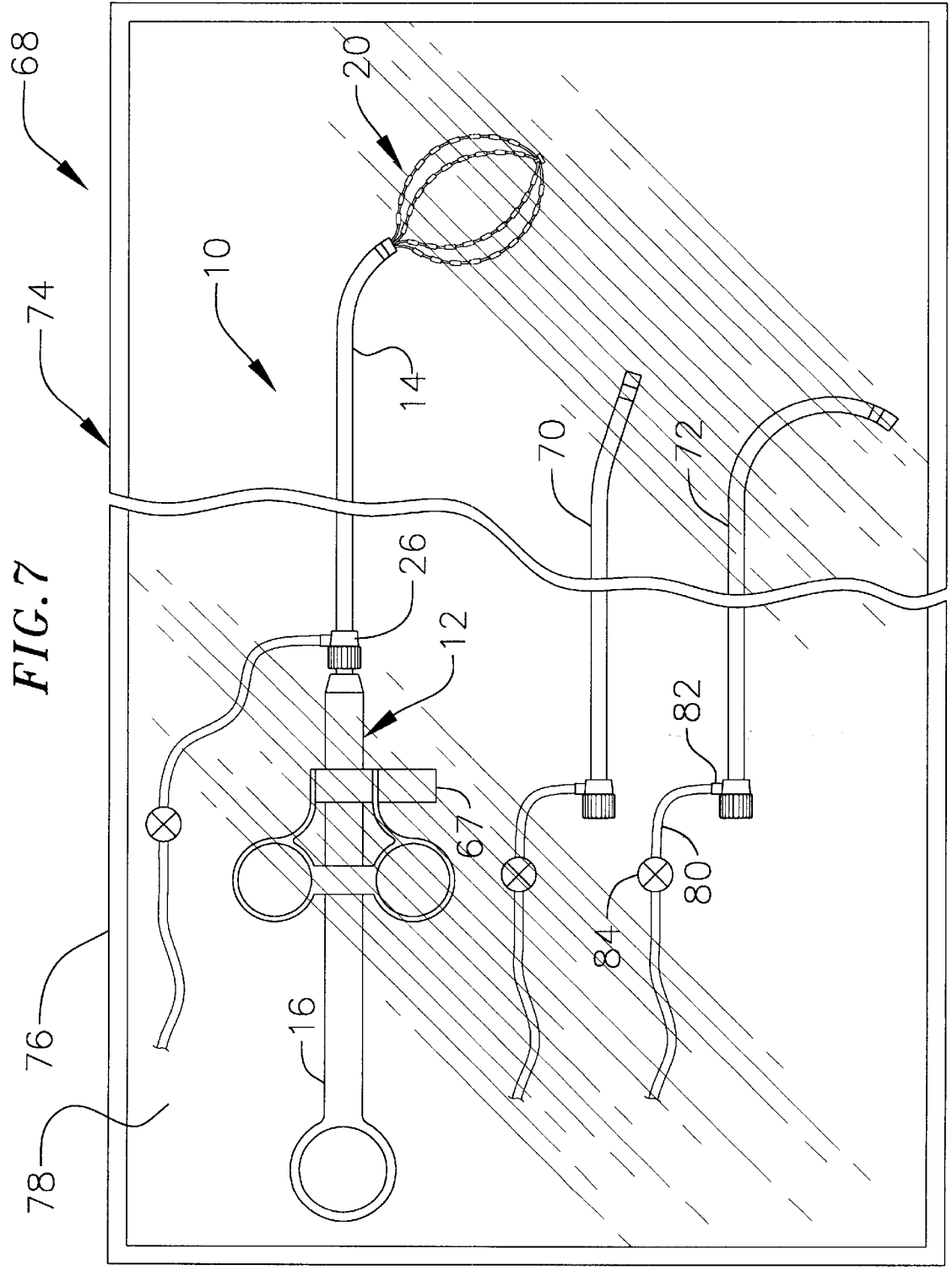
FIG. 7 is a plan view of a procedure kit in accordance with preferred embodiment of a present invention.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Applications
II. Probe Assemblies
III. Procedure Kits

The section titles and overall organization of the present detailed description are for the purpose of convenience only and are not intended to limit the present inventions.

I. Applications

The present inventions may be in the form of catheter-based probes used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of conditions within the heart. The inventions herein also have application in the diagnosis or treatment of ailments of the gastrointestinal tract, prostrate, brain, gall bladder, uterus, and other regions of the body.

Nevertheless, not all implementations of the inventions are necessarily catheter-based. For example, some implementations of the inventions may encompass hand held surgical devices (or "surgical probes") with a diagnostic and/or therapeutic structure on the distal end of the probe. The diagnostic and/or therapeutic structure may be placed directly in contact with the targeted tissue area by a physician during a surgical procedure. With respect to procedures involving the heart, access may be obtained by way of a thoracotomy, median sternotomy, or thoracostomy. Exemplary surgical probes are disclosed in U.S. Pat. No. 6,142,994. Surgical probe devices in accordance with the present inventions preferably include a handle, a relatively short shaft, and one of the distal expandable/collapsible devices described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient.

II. Probe Assemblies

As illustrated for example in FIGS. 1–3, a probe assembly 10 in accordance with one embodiment of a present invention includes a diagnostic and/or therapeutic ("DT") apparatus 12 and a tubular member 14 into which the DT apparatus is inserted. In the illustrated embodiment, the DT apparatus 12 includes a handle 16, a catheter body 18 and a collapsible/expandable device 20 mounted on the distal end of the catheter body, while the tubular member 14 is preferably a sheath having a lumen through which the catheter body and collapsible/expandable device may be advanced. Each of these devices is described in greater detail below. The DT apparatus 12 and a tubular member 14 are adapted to be removably secured to one another in the manner illustrated for example in FIG. 1. So arranged, the handle 18 may be used to urge the collapsible/expandable device 20 in and out of the distal end 22 of the tubular member 14.

The descriptive phrase "removably secured" is used herein to describe situations where the DT apparatus 12 and tubular member 14 may be readily coupled and de-coupled from one another through, for example, an interlocking mechanical connection. Such situations exclude methods of permanently (or "fixedly") securing elements together, such as chemical bonding, welding and using mechanical fastening devices that are not designed or positioned in a manner that allows them to be readily unfastened by the user.

In the exemplary embodiment, the DT apparatus 12 and tubular member 14 are removably secured to one another with a luer lock arrangement that consists of a male luer fitting 24 on the DT apparatus and a female luer fitting 26 on the tubular member. The male luer fitting 24 includes a pair of external detents 28, while the female luer fitting 26 includes corresponding internal threads (not shown). The detents 28 and threads are configured such that the male luer fitting 24 and female luer fitting 26 can be locked with one-half of a turn. Of course, other devices that will removably secure the DT apparatus 12 to the tubular member 14 may also be used. For example, a tapered, friction fit arrangement may be employed.

With respect to the specific features of the exemplary DT apparatus 12, the handle 16 consists of an inner handle member 30 and an outer handle member 32, each of which is formed from molded plastic or another suitable material. The outer handle member 32 is slidably supported on the inner handle member 30 by proximal and distal base portions 34 and 36 such that the inner and outer handle members may be moved longitudinally relative to one another. The inner handle member 30 is removably secured to the tubular member 14 by way of the luer fittings 24 and 26, while the outer handle member 32 is fixedly secured to the catheter body 18 in the manner described below. As such, movement of the inner handle member 30 relative to the outer handle member 32 causes the catheter body 18 and collapsible/expandable device 20 to move relative to the tubular member 14. Relative movement is facilitated by way of a thumb aperture 38 on the inner handle member 30 and a pair of finger apertures 40 and 42 on the outer member 32 which allows the physician to proceed using one hand.

As illustrated for example in FIGS. 4–6, the inner handle member 30 is an open structure that includes a pair of side members 44 and 46 which define an open region 48 therebetween, while the outer handle member 32 includes a post 50 that slides distally and proximally between the side members. The proximal end of the catheter body 18 is fixedly secured to the post 50. Preferably, the post 50 will include an aperture into which the proximal end of the catheter 18 is inserted and either press-fit or glued in place.

It should be noted that other types of handles may be employed so long as the handle is capable of causing relative movement between the DT apparatus 12 and tubular member 14. For example, the exemplary handle 16 may be modified such that the inner handle member 30 is fixedly secured to the catheter body 18 and the outer handle member 32 is removably secured to the tubular member 14. Here, the outer member distal base portion 36 would be extended beyond the distal end of the inner handle member 30. A piston and cylinder arrangement, such as that found in the Polaris® handle manufactured by EP Technologies, Inc. in San Jose, Calif., may also be employed. The DT apparatus 12 would be fixedly secured to the Polaris® handle cylinder and tubular member 14 would be removably secured to the piston. This arrangement may also be reversed if desired. Handles that include a handle body and a rotating control device mounted thereon are also contemplated. Here, the DT apparatus 12 could be operably connected to the rotating control device and tubular member 14 could be removably secured to the handle body.

Turning next to the exemplary catheter body 18, the catheter body is preferably a tubular element formed from a flexible biocompatible thermoplastic material such as braided or unbraided Pebax® (polyether block emide), polyethylene, or polyurethane, and is about 6 French to about 9 French in diameter. The catheter body 12 may, if desired, have a two part construction consisting of a relatively short flexible distal member (formed from unbraided Pebax®) that can bend with the distal portion of the tubular member 14 and a longer less flexible proximal member (formed from braided Pebax®). Alternatively, a guide coil may be used in place of the plastic tubing.

In the exemplary embodiment illustrated in FIGS. 1–6, the collapsible/expandable device 20 is a mapping and/or coagulation basket. Such baskets typically include two to eight electrode supporting splines 52 and one to eight electrodes 54 on each spline. The exemplary embodiment includes eight splines 52 with eight electrodes 54 on each spline. The splines 52, which are preferably made of a resilient, biologically inert material such as Nitinol® metal, flat stainless steel ribbon, stranded stainless steel or silicone rubber, may be arranged either symmetrically or asymmetrically about the longitudinal axis of the basket. The splines 52 are connected between a base member 56 and an end cap 58 (or solder bead when stainless steel is employed) in a resilient, pretensed, radially expanded condition that will bend and conform to the tissue surface they contact. One example of a suitable basket and catheter arrangement is the Constellation® basket catheter manufactured by EP Technologies, Inc. in San Jose, Calif.

Another exemplary collapsible/expandable device is an inflatable microporous structure, such as one of the inflatable structures illustrated in U.S. Pat. Nos. 5,961,513 and 6,099,526, which are incorporated herein by reference. The handle 16 would have to be modified so as to include a fluid inlet/outlet port when an inflatable microporous structure is used.

Turning to the tubular member 14 illustrated in FIG. 3, the tubular member 14 is preferably a sheath formed from materials such as braided Pebax®, polyethylene, or polyurethane. The length and diameter will vary in accordance with the intended application. For cardiovascular applications employing the aforementioned Constellation® basket catheter, the length is preferably from 60 cm to 110 cm, the outer diameter is preferably from 3 mm to 4 mm and the inner diameter is preferably from 2.5 mm to 3.5 mm. The distal portion of the tubular member 14 may have a region 60 with a preset curvature formed by heat setting or other suitable techniques. The tubular member distal tip 62 is preferably softer than the remaining portion of the tubular member 14 to reduce the likelihood of tissue trauma. This may be accomplished by thermally bonding a lower durometer tip onto the distal end of the tubular member 14. A marker band 64, which is formed from a material such as platinum or gold that is visible using fluoroscopic imaging techniques, is positioned near the soft distal tip 62.

The exemplary tubular member 14 is also provided with a fluid infusion port 66 that allows fluids, such as water or saline for lubrication, to be introduced into the tubular member. A luer lock connection that can be connected to a syringe is a suitable fluid infusion port. In a preferred embodiment, the interior region of the female luer fitting 26 will include a haemostatic valve (not shown) located proximal to the fluid infusion port 66.

An electrical connector 67 may be positioned on the handle 16. A suitable connector is a 64-pin dual edge connector, such as those manufactured by AMP in Erie, Pa. Here, a re-usable ribbon cable or other suitable electrical cable (not shown) would be connected to the connector 67 and to a conventional electrophysiological mapping system. One advantage of the electrical connector 67 and re-usable cable arrangement is cost savings because a permanent cable need not be incorporated into every DT apparatus as, is the case now with many conventional diagnostic and/or therapeutic apparatus.

The electrical connector 67 is preferably mounted on the portion of the handle 16 that is connected to the catheter body 18 so that the wires (not shown) from the electrodes 54 can be easily terminated within the connector. Thus, in the illustrated embodiment, the connector 67 is mounted on the outer handle member 32. Conversely, if the catheter body 18 is secured to the inner handle member 30 as it is in one of the alternative embodiments described above, the connector 67 could, for example, be positioned on the proximal end of the thumb aperture 38.

III. Procedure Kits

As illustrated for example in FIG. 7, the exemplary probe assembly 10 illustrated in FIGS. 1–6 may be incorporated into an electrophysiological procedure kit 68. The exemplary kit 68 includes the DT apparatus 12 and a plurality of tubular members 14, 70 and 72. The tubular members 70 and 72 have different characteristics than tubular member 14. Such characteristics may include, but are not limited to, flexibility and distal region curvature. Thus, if a particular procedure or set of procedures (such as mapping each chamber of the heart) requires a few different tubular members, the DT apparatus and required tubular members may be provided in a convenient kit. The other tools and devices required for a particular procedure or set of procedures may be provided within the kit itself or provided separately.

In the preferred implementation of the kit, the tubular member that is expected to be used in the first procedure will be pre-coupled with DT apparatus in the manner illustrated in FIG. 7. Once the first procedure is complete, the physician will simply remove the probe assembly from the patient, decouple the DT apparatus from the tubular member, remove the tubular member, introduce the DT apparatus into one of the other tubular members with an introducer sheath, couple the two together, and re-introduce the probe assembly into the patient.

In the exemplary embodiment illustrated in FIG. 7, which is intended for use in mapping procedures, the tubular members 70 and 72 are essentially identical to the tubular member 14 but for the distal region curvature. The tubular members in the kit 68 may, for example, be selected from tubular members having 15, 30, 55, 120 and 140 degree distal region curvatures. The number of tubular members included in the kit 68 will, of course, depend on the procedure.

The DT apparatus 12 and tubular members 14, 70 and 72 are housed in a sterile package 74 that has a flat rigid bottom portion 76 and a top transparent top cover 78 that provides recesses for the DT apparatus, tubular members, and any other included tools. The bottom portion 76 may be formed from Tyvek® spun bonded plastic fibers, or other suitable materials, which allow the contents of the package to be sterilized after the tools are sealed within the package.

As noted above, the fluid infusion port 66 (such as a luer fitting) allows fluids, such as water or saline for lubrication, to be introduced into the tubular members 14, 70 and 72. The fluids are typically stored in a drip bag. In a preferred implementation of the kit 68, the tubular members 14, 70 and 72 are packaged with pre-attached fluid tubes 80 that can be connected to the drip bags. Each fluid tube 80 includes a female luer fitting 82 and a stop valve 84.

Although the present inventions have been described in terms of the preferred embodiment above, numerous modifications and/or additions to the above-described preferred embodiments would be readily apparent to one skilled in the art. It is intended that the scope of the present inventions extends to all such modifications and/or additions.

I claim:

1. An assembly, comprising:
   an apparatus including a catheter body defining a distal portion and a proximal portion and an expandable/collapsible device carried by the distal portion of the catheter body;
   a tubular member defining a distal portion, a proximal portion and a lumen configured to receive the apparatus; and
   a handle fixedly connected to one of the proximal portion of the catheter body and the proximal portion of the tubular member and removably connected to the other of the proximal portion of the catheter body and the proximal portion of the tubular member, the handle being configured to move at least one of the catheter body and the tubular member relative to the other of the catheter body and the tubular member.

2. An assembly as claimed in claim 1, wherein the handle is fixedly connected to the proximal portion of the catheter body and removably connected to the proximal portion of the tubular member.

3. An assembly as claimed in claim 2, wherein the handle and tubular member include respective luer fittings.

4. An assembly as claimed in claim 1, wherein the expandable/collapsible device comprises a basket including a plurality of splines and at least one electrode on each spline.

5. An assembly as claimed in claim 5, further comprising:
   an electrical connector mounted on the handle; and
   a plurality of wires respectively connecting each of the electrodes to the electrical connector.

6. An assembly as claimed in claim 1, wherein the tubular member comprises a sheath.

7. An assembly as claimed in claim 1, wherein the tubular member includes a pre-bent distal portion.

8. An assembly as claimed in claim 1, wherein the tubular member includes a fluid port.

9. An assembly as claimed in claim 1, wherein the handle comprises a first handle member and a second handle member movable relative to one another.

10. An assembly as claimed in claim 9, wherein the first and second handle members are slidable relative to one another.

11. An assembly, comprising:
    an apparatus including an elongate catheter body defining a distal portion and a proximal portion and an expandable/collapsible basket carried by the distal portion of the catheter elongate body and having a plurality of splines and a plurality of electrodes supported on each spline;
    a tubular member defining a distal portion, a proximal portion and a lumen configured to receive the apparatus, the proximal portion of the tubular member including a first mechanical fitting; and
    a handle including first and second handle members that are slidable relative to one another, the first handle member being fixedly connected to the proximal portion of the elongate catheter body and the second handle member including a second mechanical fitting configured to be removably connected to the first mechanical fitting thereby removably connecting the tubular member to the second handle member.

12. An assembly as claimed in claim 11, further comprising:
    an electrical connector mounted on the first handle member; and
    a plurality of wires respectively connecting each of the electrodes to the electrical connector.

13. An apparatus for use with a tubular member defining a distal portion, a proximal portion and a lumen and including a first connector carried by the distal portion of the tubular member, the apparatus comprising:
    a catheter body defining a distal portion and a proximal portion;
    an expandable/collapsible device carried by the distal portion of the catheter body; and
    a handle fixedly connected to the proximal portion of the catheter body and including a second connector configured to removably connect to the first connector carried by the proximal portion of the tubular member, the being handle configured to move at least one of the catheter body and the tubular member relative to the other of the catheter body and the tubular member when the first and second connectors are removably connected to one another.

14. An apparatus as claimed in claim 13, wherein the handle and tubular member include respective luer fittings.

15. An apparatus as claimed in claim 13, wherein the expandable/collapsible device comprises a basket including a plurality of splines and at least one electrode on each spline.

16. An apparatus as claimed in claim 15, further comprising:
    an electrical connector mounted on the handle; and
    a plurality of wires respectively connecting each of the electrodes to the electrical connector.

17. An assembly as claimed in claim 13, wherein the handle comprises a first handle member and a second handle member movable relative to one another.

18. An assembly as claimed in claim 17, wherein the first and second handle members are slidable relative to one another.

19. An electrophysiological procedure kit, comprising:
    first and second tubular members defining a distal portion, a proximal portion and a predetermined characteristic, the predetermined characteristic of the first tubular member being different than the predetermined characteristic of the second tubular member;

an electrophysiological apparatus including an elongate body defining a distal portion and a proximal portion, an expandable/collapsible device carried by the distal portion of the elongate body, and a handle fixedly connected to the proximal portion of the elongate body and configured to be individually removably connected to the proximal portions of the first and second tubular member, the handle being configured to move at least one of the elongate body and a removably connected tubular member relative to the other of the elongate body and the removably connected tubular member; and a sterilizable package enclosing the first and second tubular members and the electrophysiological apparatus.

20. An electrophysiological procedure kit as claimed in claim 19, wherein the first and second tubular members comprise first and second sheaths.

21. An electrophysiological procedure kit as claimed in claim 19, wherein the predetermined characteristic comprises distal portion curvature.

22. An electrophysiological procedure kit as claimed in claim 19, wherein the handle and tubular members include respective luer fittings.

23. An electrophysiological procedure kit as claimed in claim 19, wherein the elongate body comprises a catheter body.

24. An electrophysiological procedure kit as claimed in claim 19, wherein the expandable/collapsible device comprises a basket including a plurality of splines and at least one electrode on each spline.

25. An electrophysiological procedure kit as claimed in claim 24, further comprising:

an electrical connector mounted on the handle; and a plurality of wires respectively connecting each of the electrodes to the electrical connector.

26. An electrophysiological procedure kit as claimed in claim 19, wherein the handle comprises a first handle member and a second handle member movable relative to one another.

27. An electrophysiological procedure kit as claimed in claim 28, wherein the first and second handle members are slidable relative to one another.

* * * * *